US00PP24981P2

(12) United States Plant Patent
Conyers

(10) Patent No.: US PP24,981 P2
(45) Date of Patent: Oct. 21, 2014

(54) ***HIBISCUS* PLANT NAMED 'IMPROVED MANDARIN WIND'**

(50) Latin Name: *Hibiscus rosa-sinensis*
Varietal Denomination: Improved Mandarin Wind

(71) Applicant: James O. Conyers, Alva, FL (US)

(72) Inventor: James O. Conyers, Alva, FL (US)

(73) Assignee: Aris Horticulture, Inc., Barberton, OH (US)

( * ) Notice: Subject to any disclaimer, the term of this patent is extended or adjusted under 35 U.S.C. 154(b) by 164 days.

(21) Appl. No.: 13/573,839

(22) Filed: Oct. 8, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Wendy C Haas
(74) *Attorney, Agent, or Firm* — C. A. Whealy

(57) ABSTRACT

A new and distinct cultivar of *Hibiscus* plant named 'Improved Mandarin Wind', characterized by its upright, somewhat outwardly spreading, uniformly mounded and dense plant habit appropriate for container production; glossy green-colored leaves; uniform, freely and early flowering habit; large ruffled orange-colored flowers with red purple-colored centers; and good postproduction and garden performance.

2 Drawing Sheets

Botanical designation: *Hibiscus rosa-sinensis.*
Cultivar denomination: 'IMPROVED MANDARIN WIND'.

BACKGROUND OF THE INVENTION

The present invention relates to a new and distinct *Hibiscus* plant, botanically known as *Hibiscus rosa-sinensis* and hereinafter referred to by the name 'Improved Mandarin Wind'.

The new *Hibiscus* plant is a product of a planned selection program conducted by the Inventor in Alva, Fla. The objective of the selection program is to identify new freely-branching *Hibiscus* plants with a dense, uniform and compact plant habit appropriate for container production, early and uniform flowering habit, numerous flowers per lateral branch, desirable flower color and good garden performance.

The new *Hibiscus* plant is a naturally-occurring whole plant mutation of *Hibiscus rosa-sinensis* 'Mandarin Wind', disclosed in U.S. Plant patent application Ser. No. 10/156,553. The new *Hibiscus* plant was discovered and selected by the Inventor as a single flowering plant within a population of plants of 'Mandarin Wind' in a controlled greenhouse environment in Alva, Fla. in March, 2008.

Asexual reproduction of the new *Hibiscus* plant by vegetative terminal cuttings in a controlled greenhouse environment in Alva, Fla. since May, 2008 has shown that the unique features of this new *Hibiscus* plant are stable and reproduced true to type in successive generations.

SUMMARY OF THE INVENTION

Plants of the new *Hibiscus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Improved Mandarin Wind'. These characteristics in combination distinguish 'Improved Mandarin Wind' as a new and distinct *Hibiscus* plant:

1. Upright, somewhat outwardly spreading, uniformly mounded and dense plant habit appropriate for container production.
2. Glossy green-colored leaves.
3. Uniform, freely and early flowering habit.
4. Large ruffled orange-colored flowers with red purple-colored centers.
5. Good postproduction and garden performance.

Plants of the new *Hibiscus* can be compared to plants of the parent, 'Mandarin Wind'. Plants of the new *Hibiscus* differ from plants of 'Mandarin Wind' in the following characteristics:

1. Plants of the new *Hibiscus* are more freely branching than plants of 'Mandarin Wind'.
2. Plants of the new *Hibiscus* flower one to two weeks earlier than plants of 'Mandarin Wind'.

Plants of the new *Hibiscus* can be compared to plants of the *Hibiscus rosa-sinensis* 'Caroline', disclosed in U.S. Plant Pat. No. 11,779. In side-by-side comparisons conducted in Alva, Fla., plants of the new *Hibiscus* differed from plants of 'Caroline' in the following characteristics:

1. Plants of the new *Hibiscus* were more vigorous than and not as compact as plants of 'Caroline'.
2. Plants of the new *Hibiscus* had larger leaves than plants of 'Caroline'.
3. Plants of the new *Hibiscus* had larger flowers than plants of 'Caroline'.
4. Flower petals of plants of the new *Hibiscus* were ruffled whereas flower petals of plants of 'Caroline' were not ruffled.
5. Plants of the new *Hibiscus* and 'Caroline' differed in flower color as plants of 'Caroline' had orange-colored flowers with orange-colored centers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Improved Mandarin Wind' grown in a container.

The photograph on the second sheet comprises a close-up view of a typical flowering plant of 'Improved Mandarin Wind'.

DETAILED BOTANICAL DESCRIPTION

The aforementioned photographs and following observations, measurements and values describe plants grown during the summer in 15-cm containers in a fiberglass-covered greenhouse in Alva, Fla. and under cultural practices which closely approximate commercial *Hibiscus* production. During the production of the plants, day temperatures ranged from 20° C. to 38° C., night temperatures ranged from 15° C. to 24° C. and light levels ranged from 3,000 to 4,000 foot-candles. Plants were pinched two times and were 27 weeks old when the photographs and the description were taken. In the description, color references are made to The Royal Horticultural Society Colour Chart, 2007 Edition, except where general terms of ordinary dictionary significance are used.

Botanical classification: *Hibiscus rosa-sinensis* 'Improved Mandarin Wind'.

Parentage: Naturally-occurring whole plant mutation of *Hibiscus rosa-sinensis* 'Mandarin Wind', disclosed in U.S. Plant patent application Ser. No. 10/156,553.

Propagation:

- *Type*.—By vegetative terminal cuttings.
- *Time to initiate roots*.—About 10 days at temperatures of 24° C.
- *Time to develop roots*.—About four weeks at temperatures of 24° C.
- *Root description*.—Thick, fibrous; white in color.
- *Rooting habit*.—Moderately freely branching; medium density.

Plant description:

- *Plant form and growth habit*.—Perennial, evergreen, upright, somewhat outwardly spreading, compact, uniformly mounded and dense; moderately vigorous to vigorous growth habit.
- *Branching habit*.—Freely branching habit with lateral branches potentially develop at every node; pinching enhances lateral branch development.
- *Plant height*.—About 26 cm.
- *Plant diameter* (*area of spread*).—About 39 cm.

Lateral branch description:

- *Length*.—About 14.5 cm.
- *Diameter*.—About 7 mm.
- *Internode length*.—About 2.3 cm.
- *Aspect*.—Upright to outwardly spreading.
- *Texture*.—Immature, smooth; mature, woody and rough.
- *Color, immature*.—Close to 144A.
- *Color, mature*.—Close to 197B to 197C.

Foliage description:

- *Arrangement*.—Alternate, single; numerous; symmetrical.
- *Length*.—About 8.75 cm.
- *Width*.—About 8.25 cm.
- *Shape*.—Cordate.
- *Apex*.—Acute.
- *Base*.—Cordate.
- *Margin*.—Crenate with truncate tendencies.
- *Texture, upper and lower surfaces*.—Smooth, glabrous.
- *Luster, upper surface*.—Glossy.
- *Luster, lower surface*.—Somewhat glossy.
- *Venation pattern*.—Pinnate; arcuate.
- *Color*.—Developing leaves, upper surface: Close to N137A. Developing leaves, lower surface: Close to 137B. Fully expanded leaves, upper surface: Close to 147A; venation, close to 147A. Fully expanded leaves, lower surface: Close to 137B; venation, close to 144A.
- *Petioles*.—Length: About 3.8 cm. Diameter: Proximally, about 4 mm. Texture, upper and lower surfaces: Slightly pubescent. Color, upper and lower surfaces: Close to 144A.

Flower description:

- *Flower arrangement and flowering habit*.—Rotate star-shaped flowers arranged at terminal leaf axils; uniform and freely flowering habit with about two or three flowers per terminal; flowers face mostly upright to outwardly.
- *Natural flowering season*.—Plants of the new *Hibiscus* flower naturally during the spring and summer or during periods of warm weather; plants flower year-round in the greenhouse.
- *Flower longevity*.—Flowers last about two to three days on the plant; flowers persistent.
- *Flower diameter*.—About 12.5 cm.
- *Flower length* (*height*).—About 8.5 cm.
- *Flower buds*.—Resistance to abscission during shipping: Plants of the new *Hibiscus* have been observed to resist flower bud drop when stored in a closed box for five days at 13° C. Length: About 2 cm. Diameter: About 1.1 cm. Shape: Ovoid. Color: Darker green than 144A.
- *Petals*.—Arrangement: Corolla consists of five petals that are fused at base; petals imbricate. Length: About 7.5 cm. Width: About 7 cm. Shape: Roughly spatulate. Apex: Rounded. Base: Attenuate. Margin: Entire; slightly undulate, ruffled appearance. Texture: Smooth, glabrous; velvety; veins prominent on the lower surface. Color: When opening and fully opened, upper surface: Close to between 31A and 32A; towards the base, close to 49A; at the base, close to 53A. When opening and fully opened, lower surface: Close to 25D tinged with close to between 31A and 32A; towards the base, close to 49A to 49D.
- *Sepals*.—Appearance: Five sepals fused into a tubular star-shaped calyx. Length: About 2.5 cm. Width: About 1 cm. Shape: Lanceolate. Apex: Sharply acute. Margin: Entire. Texture, upper surface: Smooth, glabrous; waxy. Texture, lower surface: Slightly pubescent. Color, upper and lower surfaces: Close to 144A.
- *Bracts*.—Appearance: About seven or eight fused at base. Length: About 1.5 cm. Width: About 5 mm. Shape: Lanceolate. Apex: Acute. Margin: Entire. Texture, upper and lower surfaces: Smooth, glabrous. Color, upper and lower surfaces: Darker green than 146A.

*Peduncles*.—Length: About 2.3 cm. Diameter: About 2.25 mm. Aspect: Upright to slightly outward. Strength: Strong, flexible. Texture: Smooth, glabrous. Color: Close to 144A.

*Reproductive organs*.—Androecium: Stamen number: Numerous, about 50 per flower. Filament length: About 6.5 mm. Filament color: Close to 49A. Anther shape: Oblong. Anther length: About 1 mm. Anther color: Close to 9A. Amount of pollen: Moderate. Pollen color: Close to 13A. Gynoecium: Pistil number: One per flower. Pistil length: About 8.4 cm. Style length: About 7.6 cm. Style texture: Smooth, glabrous; waxy. Style color: Close to 39A to 39B. Stigma appearance: Five-parted, rounded. Stigma color: Close to 46A. Ovary color: Close to 11D.

*Seeds and fruits*.—Seed and fruit production has not been observed on plants of the new *Hibiscus*.

Garden performance: Plants of the new *Hibiscus* have been observed to have good garden performance and to tolerate wind, rain and temperatures ranging from about 1° C. to about 38° C.

Pathogen & pest resistance: Plants of the new *Hibiscus* grown under Florida production conditions have not been shown to be susceptible to pathogens common to *Hibiscus* such as *Pseudomonas, Pythium* and *Phytophthora*. Plants of the new *Hibiscus* have not been observed to be resistant to pests and other pathogens.

It is claimed:

1. A new and distinct *Hibiscus* plant named 'Improved Mandarin Wind' as illustrated and described.

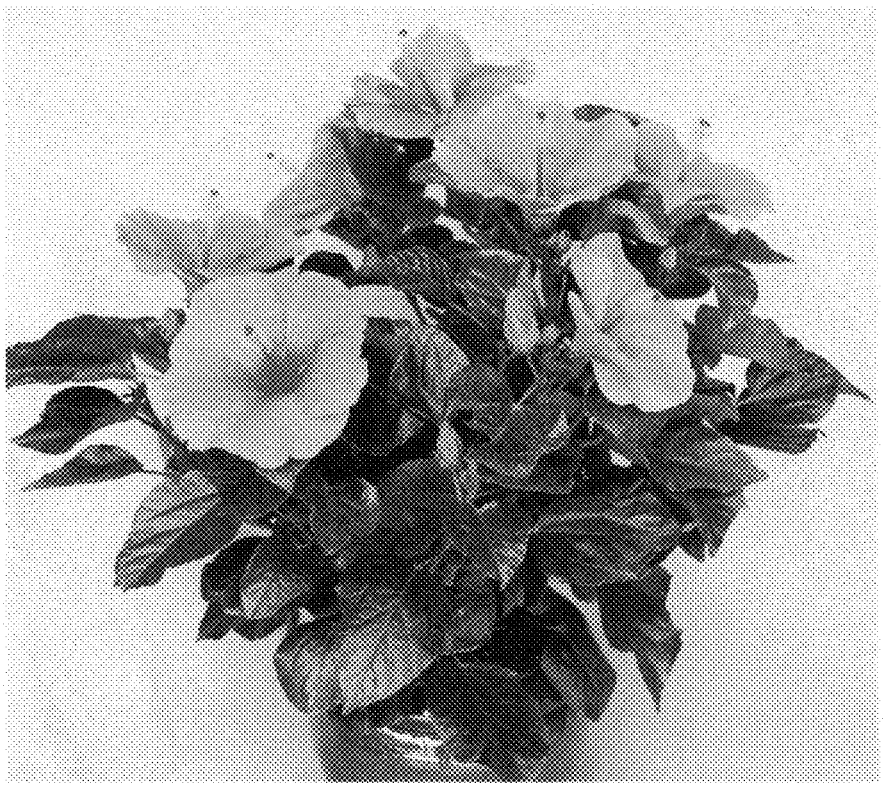

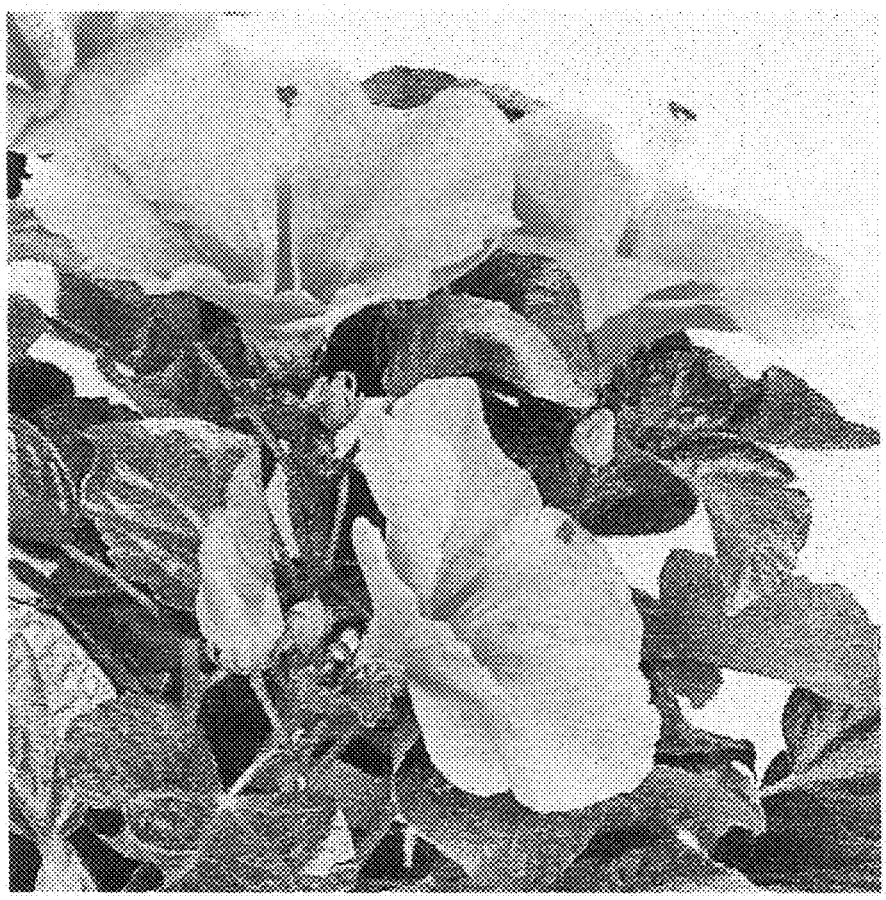

* * * * *